(12) United States Patent
Alessi et al.

(10) Patent No.: US 12,329,530 B2
(45) Date of Patent: Jun. 17, 2025

(54) HEALTH STATE MONITORING DEVICE AND METHOD

(71) Applicant: STMicroelectronics S.r.l., Agrate Brianza (IT)

(72) Inventors: Enrico Rosario Alessi, Catania (IT); Marco Leo, Milan (IT); Luca Gandolfi, Milan (IT); Fabio Passaniti, Syracuse (IT); Marco Castellano, Pavia (IT)

(73) Assignee: STMicroelectronics S.r.l., Agrate Brianza (IT)

( * ) Notice: Subject to any disclaimer, the term of this patent is extended or adjusted under 35 U.S.C. 154(b) by 336 days.

(21) Appl. No.: 17/870,172

(22) Filed: Jul. 21, 2022

(65) Prior Publication Data

US 2023/0048422 A1 Feb. 16, 2023

(30) Foreign Application Priority Data

Jul. 30, 2021 (IT) .......................... 102021000020627

(51) Int. Cl.
*A61B 5/308* (2021.01)
*A61B 5/0205* (2006.01)
(Continued)

(52) U.S. Cl.
CPC ............ *A61B 5/308* (2021.01); *A61B 5/0205* (2013.01); *A61B 5/024* (2013.01); *A61B 5/11* (2013.01);
(Continued)

(58) Field of Classification Search
CPC ................................ A61B 5/308; A61B 5/352
(Continued)

(56) References Cited

U.S. PATENT DOCUMENTS

2008/0021336 A1\* 1/2008 Dobak ................. A61B 5/1102
600/508
2008/0300497 A1 12/2008 Krause et al.
(Continued)

FOREIGN PATENT DOCUMENTS

EP 2980609 A1 2/2016
EP 3536231 A1 9/2019
(Continued)

OTHER PUBLICATIONS

An et al., "Comparison of Motion Artefact Reduction Methods and the Implementation of Adaptive Motion Artefact Reduction in Wearable Electrocardiogram Monitoring," *Sensors* 20: 1468, Mar. 2020. (21 pages).
(Continued)

*Primary Examiner* — Nadia A Mahmood
(74) *Attorney, Agent, or Firm* — Seed IP Law Group LLP

(57) ABSTRACT

A device for monitoring the health state is made in a chip including a semiconductor die integrating an electric potential sensor and a cardiac parameter determination unit. The potential sensor is configured to detect potential variations on the body of a living being and associated with a heart rhythm and to generate a cardiac signal. The cardiac parameter determination unit is configured to receive the cardiac signal and determine cardiac parameters indicative of a health state. In particular, the cardiac parameter determination unit is configured to detect triggering events and to determine features of the cardiac signal in time windows defined by the triggering events. The die also integrates a decision unit, configured to receive the cardiac parameters and generate a health signal based on a comparison with threshold values. The cardiac parameters include heart rate and QRS-complex.

19 Claims, 11 Drawing Sheets

(51) Int. Cl.
  *A61B 5/024*  (2006.01)
  *A61B 5/11*  (2006.01)
  *A61B 5/352*  (2021.01)
  *A61B 5/366*  (2021.01)

(52) U.S. Cl.
  CPC .............. *A61B 5/352* (2021.01); *A61B 5/366* (2021.01); *A61B 2562/0219* (2013.01); *A61B 2562/028* (2013.01)

(58) Field of Classification Search
  USPC ......................................................... 600/301
  See application file for complete search history.

(56) References Cited

U.S. PATENT DOCUMENTS

| | | |
|---|---|---|
| 2013/0085405 A1 | 4/2013 | Bera et al. |
| 2014/0232516 A1 | 8/2014 | Stivoric et al. |
| 2016/0157781 A1 | 6/2016 | Baxi et al. |
| 2016/0342781 A1 | 11/2016 | Jeon |
| 2019/0117985 A1 | 4/2019 | Cao et al. |

FOREIGN PATENT DOCUMENTS

| | | |
|---|---|---|
| JP | 2015156936 A | 9/2015 |
| KR | 20110061750 A | 6/2011 |

OTHER PUBLICATIONS

Ha et al., "Convolutional neural networks for human activity recognition using multiple accelerometer and gyroscope sensors," *International Joint Conference on Neural Networks (IJCNN)*, Vancouver, BC, Canada, Jul. 24-29, 2016, pp. 381-388.

Politi et al., "Human motion detection in daily activity tasks using wearable sensors," *European Signal Processing Conference (EUSIPCO)*, Lisbon, Portugal, Sep. 1-5, 2014, pp. 2315-2319.

\* cited by examiner

```
If | XL | < 1.2g
    → STATUS_0 (steady)
Else
    If HR < 60bpm
        If 80 msec < QRS < 100 msec
            → STATUS_B_Q-N (Bradycardia, Normal)
        Else
            If QRS < 60 msec
                → STATUS_B_Q-A (Bradycardia, Abnormal)
            Else
                If 60 msec < QRS < 80 msec
                    → STATUS_B_Q-CL (Bradycardia, Control-limit)
                Else
                    If 100 msec < QRS < 120 msec
                        → STATUS_B_Q-CL (Bradycardia, Control-limit)
                    Else
                        → STATUS_B_Q-A (Bradycardia, Abnormal)
                    End
                End
            End
        End
    Else
        If 60bpm < HR < 100 bpm
            If 80 msec < QRS < 100 msec
                → STATUS_N_Q-N (Normal, Normal)
            Else
                If QRS < 60 msec
                    → STATUS_N_Q-A (Normal, Abnormal)
                Else
                    If 60 msec < QRS < 80 msec
                        → STATUS_N_Q-CL (Normal, Control-limit)
                    Else
                        If 100 msec < QRS < 120 msec
                            → STATUS_N_Q-CL (Normal, Control-limit)
                        Else
                            → STATUS_N_Q-A (Normal, Abnormal)
                        End
                    End
                End
            End
        Else
            If HR > 100 bpm
                If 80 msec < QRS < 100 msec
                    → STATUS_T_Q-N (Tachycardia, Normal)
                Else
                    If QRS < 60 msec
                        → STATUS_T_Q-A (Tachycardia, Abnormal)
                    Else
                        If 60 msec < QRS < 80 msec
                            → STATUS_T_Q-CL (Tachycardia, Control-limit)
                        Else
                            If 100 msec < QRS < 120 msec
                                → STATUS_T_Q-CL (Tachycardia, Control-limit)
                            Else
                                → STATUS_T_Q-A (Tachycardia, Abnormal)
                            End
                        End
                    End
                End
            End
        End
    End
End
```

FIG. 16

HEALTH STATE MONITORING DEVICE AND METHOD

BACKGROUND

Technical Field

The present disclosure relates to a health state monitoring device and method.

Description of the Related Art

As is known, the detection of cardiac parameters in a living being represents one of the basic tools for verifying their health state.

To this end, an electrocardiographic plot or electrocardiogram (ECG) is commonly used which exploits the electric fields on the body, due to the periodic depolarizations and re-polarizations of the heart. In fact, from the electrical point of view, the heart is equivalent to an electric dipole which generates a variable voltage on the body. This voltage is directly detectable through electrodes applied to the body and able to provide a corresponding electrical signal. Therefore, certain cardiac parameters, such as, for example, the heart rate (also called beat) and the durations of specific intervals, may be measured on the basis of the plot.

For more than a hundred years, in medical practice, the ECG has been obtained using more or less bulky machines, called electrocardiographs, which transform the potential variations associated with cardiac activity into the electrocardiographic plot, printed on standard graph paper, to allow easy measurements.

Such electrocardiographs are typically used for human use and also in the veterinary field, in particular in case of mammals.

Wearable devices have also already been proposed to allow a patient cardiac activity to be monitored even outside the hospital or medical practice setting. These devices are capable of acquiring and storing the electrical signal associated with cardiac activity, as well as to measure the main parameters thereof.

For example, there are patch-shaped monitoring devices on the market, which are applied to the body and comprise electrodes. These patches also comprise a battery for supplying the device and a transmission unit, for example of wireless type, for communicating with an external processing device. The external device may provide information on the patient health state on the basis of the received signals and of particular algorithms.

However, these devices have proved not to be completely reliable, as the monitored signal is strongly affected by the state of movement of the monitored living being. In particular, the movement of the monitored living being may cause the presence of artifacts that are not easy to recognize and distinguish from the beats and therefore may be interpreted incorrectly.

To solve this problem, it has already been proposed to associate a motion detection unit, such as an accelerometer, with the wearable device and/or to introduce filters to filter out components at frequencies that are different from cardiac muscle typical frequency, at rest or under stress.

However, these components entail an undesirable increase in the size of the devices and therefore cannot be introduced into the wearable device; furthermore, they still fail to completely remove artifacts.

BRIEF SUMMARY

In various embodiments, the present disclosure provides a monitoring device which at least partially overcomes the drawbacks of the prior art.

According to the present disclosure, a health state monitoring device and method are provided.

In at least one embodiment, a device of monitoring the health state is provided that includes a semiconductor die. The semiconductor die includes an electric potential sensor configured to detect potential variations present on a body of a living being and associated with a heart rhythm and to generate a cardiac signal, and cardiac parameter determination circuitry configured to receive the cardiac signal and determine cardiac parameters indicative of a health state. The cardiac parameter determination circuitry is configured to detect triggering events and to determine features of the cardiac signal in time windows defined by the triggering events.

In at least one embodiment, an electronic apparatus is provided that includes the health monitoring device and one or more electrodes configured to detect the cardiac signal. The electrodes are electrically coupled to the electric potential sensor.

In at least one embodiment, a method of monitoring health using a health monitoring device integrated into a semiconductor material die is provided. The method includes: detecting electric potential variations on a body of a living being and associated with a heart rhythm; generating a cardiac signal; and determining cardiac parameters indicative of a health state on the basis of the cardiac signal. Determining cardiac parameters includes detecting triggering events and detecting features of the cardiac signal in time windows defined by the triggering events.

BRIEF DESCRIPTION OF THE SEVERAL VIEWS OF THE DRAWINGS

For a better understanding of the present disclosure, some embodiments thereof are now described, purely by way of non-limiting example, with reference to the attached drawings, wherein:

FIG. 16 shows a possible code usable by a decision unit belonging to the health state monitoring device of FIG. 6;

DETAILED DESCRIPTION

Hereinafter, reference will be made to a device for monitoring the health state of a person, on the basis of cardiac parameters. However, the described device is also usefully usable for health monitoring in the veterinary field, for example for mammals, therefore the reference to "people" is not to be understood as limiting, and the expression "body of a person" is to be understood as covering the body of animals as well, with obvious adjustments as to reference values and cardiac parameters.

Furthermore, although the following description refers to the monitoring of heart rate HR and QRS-interval, other parameters may be monitored, as described in detail hereinbelow.

Again, in the description below, and in a manner that is known to the person skilled in the art, the division into the shown functional blocks has an illustrative purpose only and represents only one of the possible solutions; therefore the different described functions may be grouped differently and the certain functions may be performed by different functional blocks, in particular a previous or subsequent functional block in the processing sequence, on the basis of the preferences of the designer, in a manner that is obvious to the person skilled in the art.

Figure 1:
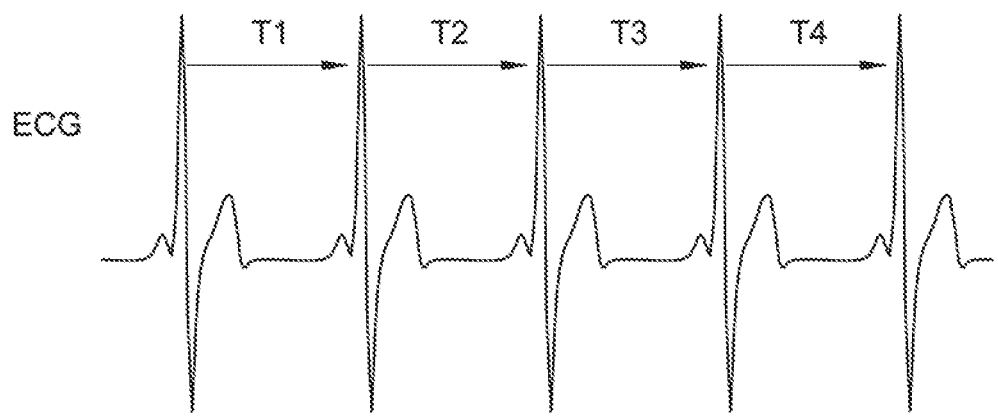
FIG. 1 shows an example of electrocardiographic plot (ECG) acquired in a human patient.

With reference to Figures, FIG. 1 shows an example of an electrocardiographic plot as detected through a cardiograph. As known, and visible in FIG. 1, the plot comprises a series of cycles having similar trend, which have typical peaks and valleys, used for measuring cardiac parameters. For example, each cycle has an easily recognizable maximum peak, normally used to detect the heart rate (or "heartbeat"), traditionally measured as the number of such peaks in one minute and generally identified by the abbreviation HR (Heart Rate).

FIG. 1 highlights the period or duration T1, T2, . . . of some cycles of the electrocardiographic plot of FIG. 1.

Figure 2:
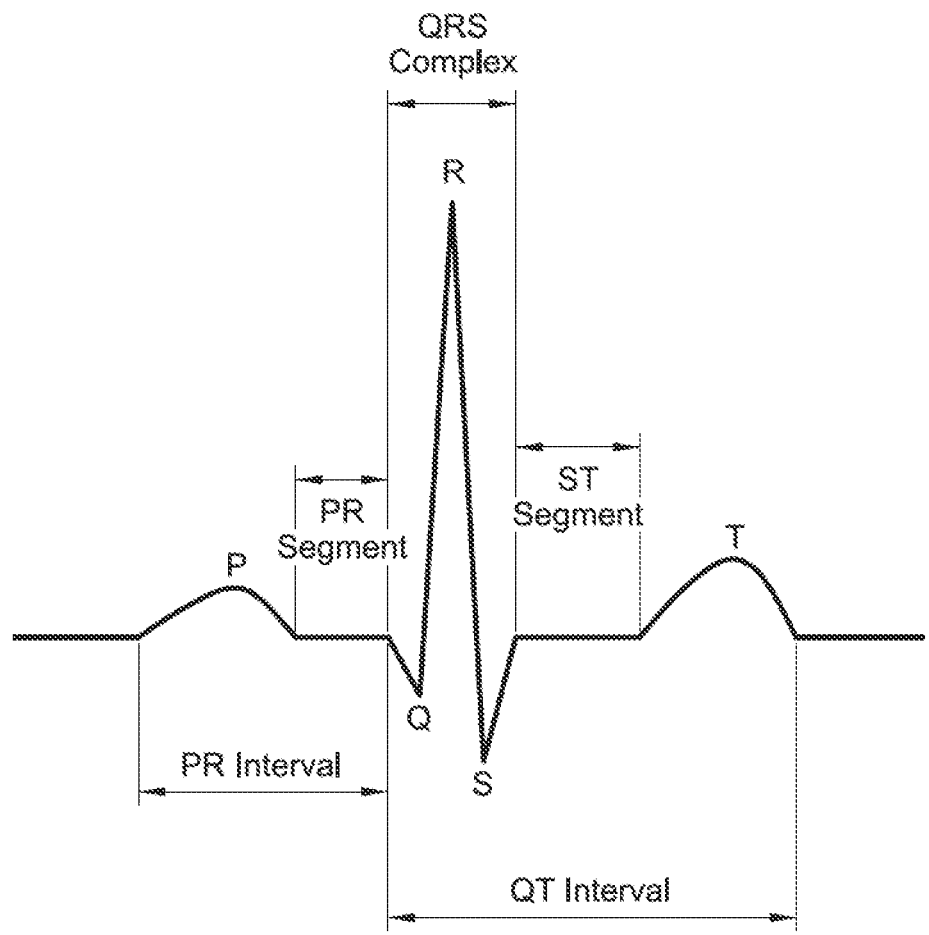
FIG. 2 shows a portion of the electrocardiographic plot of FIG. 1, relating to a cardiac cycle and highlighting the main phases.

FIG. 2 shows a single cardiac cycle on a time-enlarged scale. As visible, the cycle is characterized by a series of positive peaks, traditionally identified by the letters P, R and T and representing the maxima of respective waves of the same name, among which a series of negative peaks are present, traditionally identified by the letters Q and S and representing the minima of respective waves of the same name, as well as by flat sections (so-called PR and ST segments).

Of these, a particularly important parameter in the health evaluation is the duration of the section comprised between the beginning of the wave Q and the end of the wave S, called "QRS interval," corresponding to the depolarization time of the heart ventricles.

FIG. 2 highlights other important parameters in the cardiac cycle, including the PR interval, the QT interval, the PR segment, and the ST segment.

Figure 6:
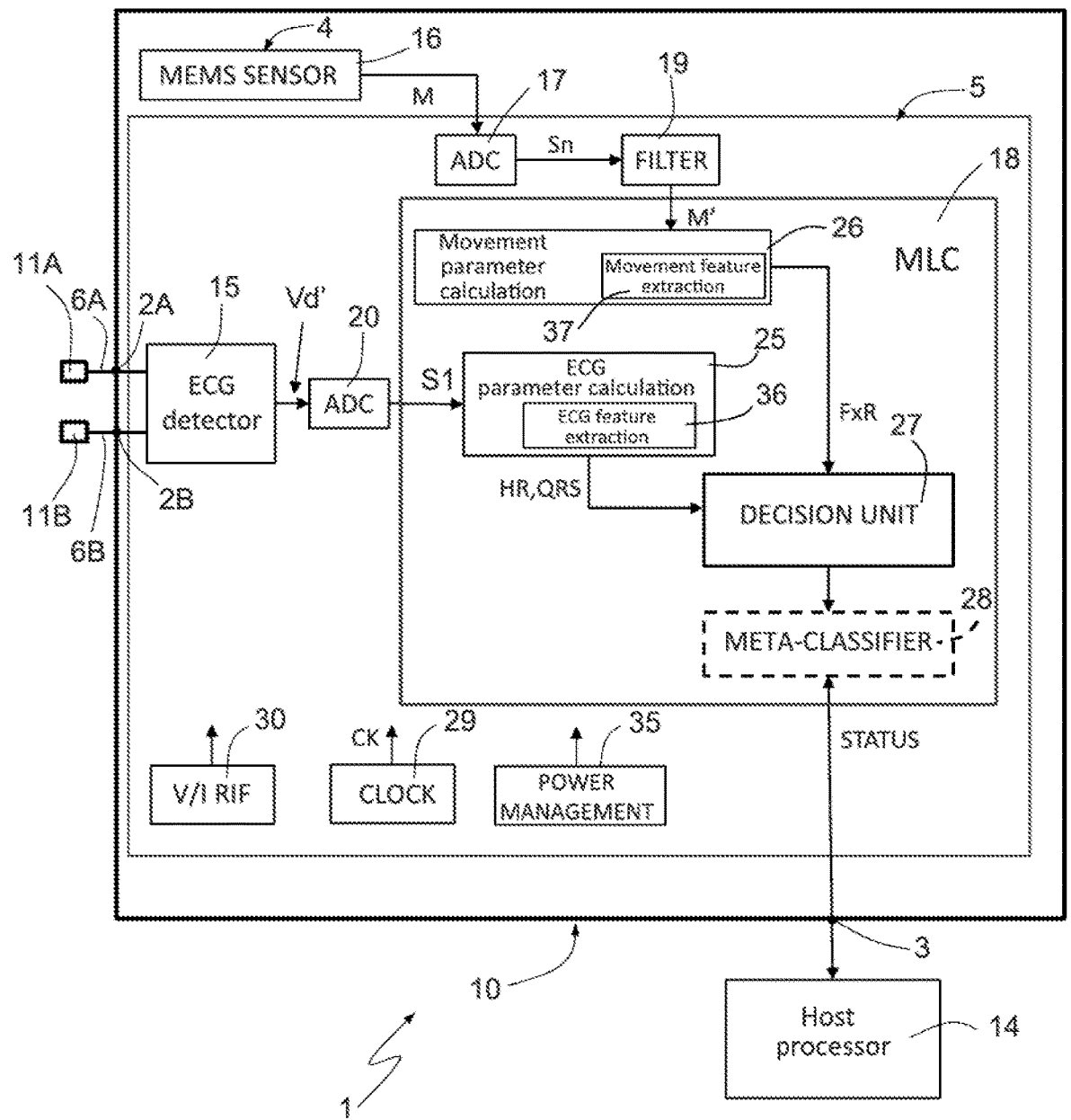
FIG. 6 is a block diagram of a device for monitoring the health state of a living being, on the basis of the electrical signal of FIG. 3.

FIG. 6 shows a health monitoring device based on the detection of cardiac parameters from an electrical signal (electrocardiographic signal, hereinafter referred to as ECG signal) detected on a person's body. Hereinafter, the device will be referred to as monitoring device 1.

In this regard it is worth noting that, although in the acquisition of the electrocardiographic plot through a traditional electrocardiograph the electrodes are to be placed in specific points of the body to obtain a normalized plot, the main parameters, such as the heartbeat, but in general the whole trend of the cardiac cycle, may be detected all over the body.

In the monitoring device 1 being described, therefore, the heart rate and the other monitored parameters may be obtained from measurements taken in various parts of the body, for example on the wrist, on the side of the neck, on the back of the knees, on the top of the foot, at groin or on the fingers, using common or suitably arranged electrodes, as discussed hereinbelow.

With reference to FIG. 6, the monitoring device 1 is a packaged device, comprising a first die 4, of semiconductor material, integrating a MEMS sensor, and a second die 5, of semiconductor material, forming an ASIC ("Application-Specific Integrated Circuit") and implementing different functions, as described below.

The first and the second dice 4, 5 are arranged in a single case or package and form a chip 10 having here a pair of inputs 2A, 2B and one output 3.

The inputs 2A, 2B are configured to be coupable to a respective external connector 11A, 11B through a respective line 6A, 6B.

For example, the lines 6A, 6B may be conductive wires or tracks on a printed circuit board (not shown) and connect two pins of the chip 10 (forming the inputs 2A, 2B) to the respective external contact 11A, 11B.

Figure 7:
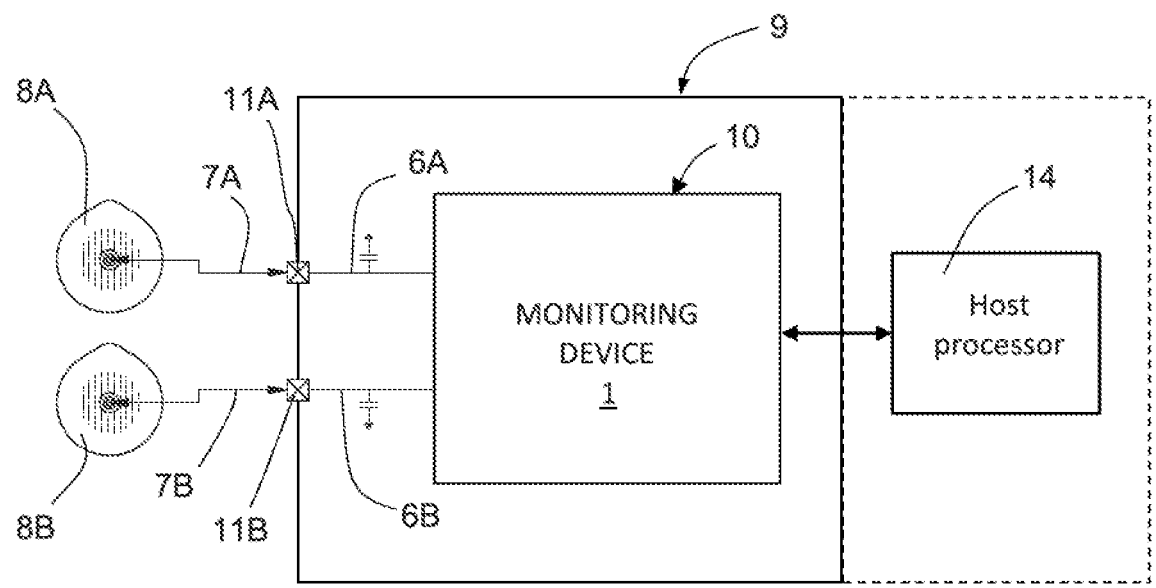
FIG. 7 shows a possible application of the present health state monitoring device in an apparatus having electrodes for detecting the electrocardiographic signal of FIG. 3 on the body of a person.

According to a possible implementation, shown in FIG. 7, the chip 10 may be accommodated in a housing 9, for example of a monofunctional monitoring apparatus. Alternatively, the housing 9 may be bonded on an adhesive patch provided with electrodes, directly applicable to a person body.

In both cases, the external contacts 11A, 11B may be female connectors of a jack type or male/female buttons or the like, accessible from the outside of the housing 9 and coupeable, through respective female/male connectors (not shown), to wires 7A, 7B. The wires 7A, 7B are in turn attached or may be coupled to disposable electrodes 8A, 8B, as shown in FIG. 7. Alternatively, the external contacts 11A, 11B may be fixed connections, soldered to a printed circuit board (not shown) inside the housing 9, and the wires 7A, 7B protrude directly from the housing 9.

Figure 8:
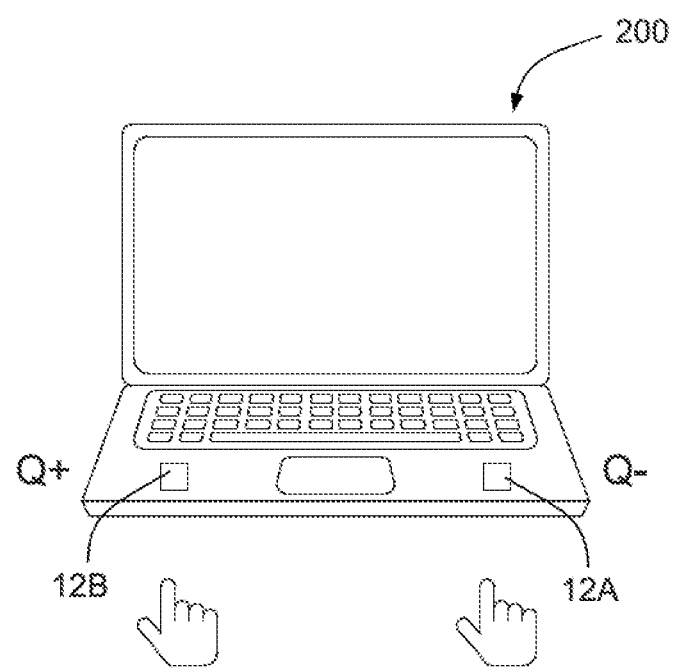
FIG. 8 shows a different application of the present health state monitoring device inside a portable computer.

According to a different embodiment, shown in FIG. 8, the chip 10 is accommodated in a personal computer 200, for example a portable computer, a laptop, a notebook, a tablet or the like.

Here, the personal computer 200 has two pads 12A and 12B forming the external contacts 11A, 11B of FIG. 6. In this case, as explained below, the acquisition of the electrocardiographic signal may occur by placing two fingers on the pads 12A, 12B.

In FIG. 6, the output 3 may be an external connector or a transmission unit for wireless connection to an external processor (host processor) 14 provided for example with a BLE (Bluetooth Low Energy) connection unit or with an optical signaling unit (for example one or more LEDs) configured to display the monitoring result or to highlight normal/abnormal parameters by emitting light of different colors.

For example, in case of a monitoring device 1 accommodated in the housing 9 (FIG. 7), the external processor 14 may be accommodated in the same housing 9; alternatively it may be external thereto, as shown by dashed lines.

If the monitoring device 1 is accommodated in the personal computer 200 of FIG. 8, the external processor 14 may be the central unit or a processor of the personal computer 200.

With reference again to FIG. 6, the monitoring device 1 comprises an electrocardiographic signal detector (ECG detector 15); an ECG analog-to-digital converter 20; a movement sensor 16; a movement analog-to-digital converter (ADC) 17; a filtering unit 19; a processing unit 18; and some auxiliary blocks that perform common functions useful for the monitoring device 1, coupled to blocks 15-20. For example, the auxiliary blocks here comprise a clock circuit 29, including an internal oscillator and intended to generate a clock signal CK; a reference current/voltage generation block 30; and a power management block 35, having the function of suitably supplying the other blocks.

The ECG detector 15 is an electric potential detector able to detect potential variations on a person body, due to cardiac activity.

Figure 9:
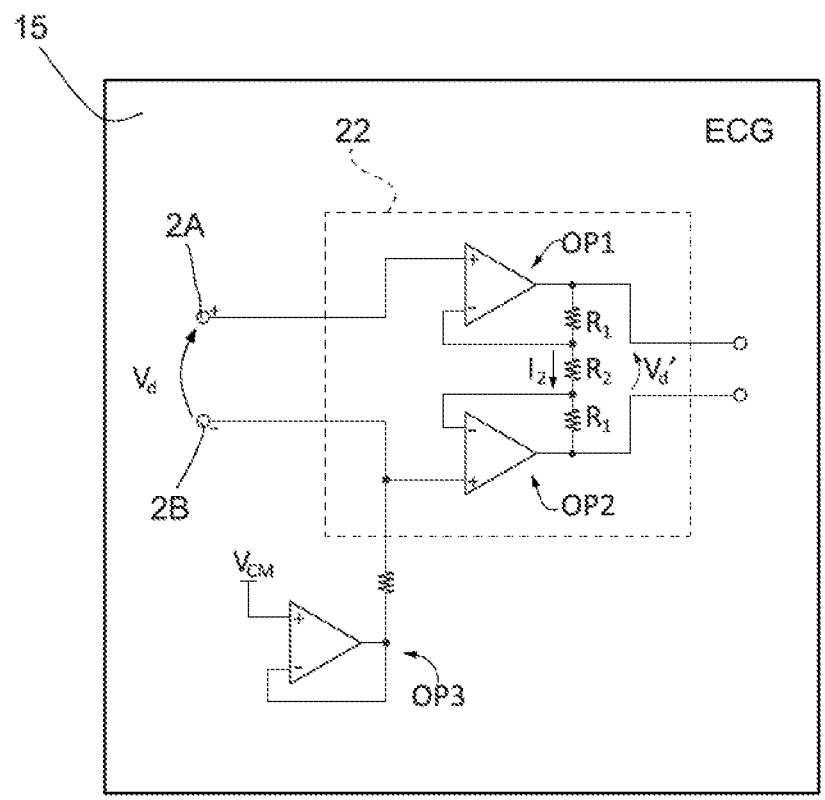
FIG. 9 is a simplified electrical diagram of an implementation of an electric potential sensor provided in the health state monitoring device of FIG. 6.

For example, the ECG detector 15 may be made as shown in FIG. 9.

The ECG detector 15 of FIG. 9 comprises an amplifier stage 22 having inputs connected to the inputs 2A, 2B of the monitoring device 1 and receiving, in operating condition, an input voltage Vd corresponding to the potential difference between external contacts 11A, 11B and therefore between two different points on the body of the monitored person.

The amplifier stage 22 comprises, according to an exemplary embodiment, a first and a second operational amplifier OP1 and OP2 and a biasing stage (buffer) OP3 which has the function of biasing the amplifier stage 22 to a common mode voltage VCM.

In detail, the operational amplifiers OP1, OP2 have non-inverting terminals coupled to the first and, respectively, to the second inputs 2A, 2B of the monitoring device 1 and inverting terminals coupled to the respective outputs through respective feedback resistors R1.

The non-inverting input of the second operational amplifier OP2 is also coupled to the buffer OP3.

Furthermore, the inverting terminals of the first and the second operational amplifiers OP1, OP2 are mutually coupled through an amplification resistor R2 receiving, in operating condition, a voltage equal to the input voltage Vd; therefore, in this condition, a current I2=Vd/R2 flows through the amplification resistor R2.

The current I2 does not come from the input terminals of the operational amplifiers OP1, OP2 and therefore flows through the two feedback resistors R1 coupled in series with the amplification resistor R2; therefore the current I2, flowing through the series-coupled resistors R1-R2-R1 produces an output voltage Vd':

$$Vd'=(2R1+R2)I2=(2R1+R2)Vd/R2.$$

Therefore, the amplifier stage 22 has an overall gain Ad:

$$Ad=Vd'/Vd=(2R1+R2)/R2=1+2R1/R2.$$

The output voltage Vd' is therefore proportional to the potential Vd between the inputs 2A, 2B of the monitoring device 1; in particular it has a trend following the potential variation on a patient body, due to the cardiac activity.

Figure 3:
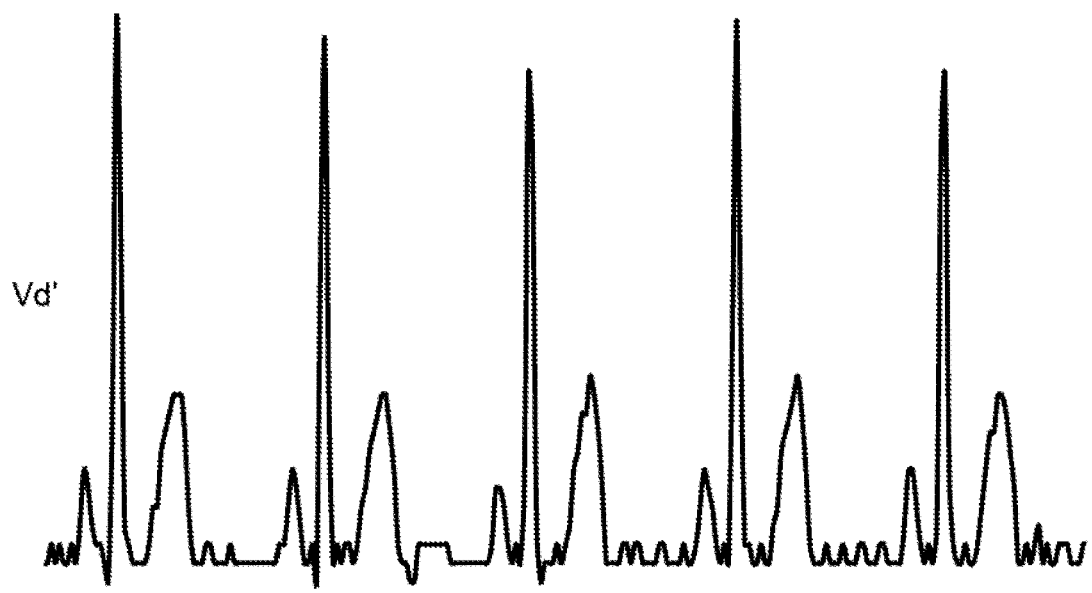
FIG. 3 shows the trend of an electrical signal forming an electrocardiographic signal used herein.

For example, FIG. 3 shows the trend of the output voltage Vd' of the ECG detector 15.

Returning to FIG. 6, the output voltage Vd' of the ECG detector 15 is supplied to the input of the ECG analog-to-digital converter 20, which outputs an ECG signal S1 formed by a plurality of samples, in a per se known manner. In a way not shown, in the ECG analog-to-digital converter 20, a normalization circuit may be provided downstream of the digitization circuits, for removing the offset of the ECG signal S1.

The movement sensor 16 is a MEMS (Micro-Electro-Mechanical-System) sensor of inertial type, comprises, for example, an accelerometer and/or a gyroscope, and is configured to output one or more movement signals M. For example, the MEMS sensor may be a three-dimensional accelerometer outputting three displacement signals X, Y, Z (along three perpendicular axes), hereinafter also identified as a whole as displacement signals XL. Furthermore, the MEMS sensor may be a triaxial gyroscope and provide three rotation signals $\Omega X$, $\Omega Y$ and $\Omega Z$ (around three perpendicular axes), hereinafter also identified as a whole as rotation signals $\Omega$.

In a manner not shown, the MEMS sensor 16 may include signal amplification circuits.

In use, the movement signals M are provided to the movement analog-to-digital converter 17 and, therefrom, to the filtering unit 19, configured to output filtered movement signals M'.

Figure 10:
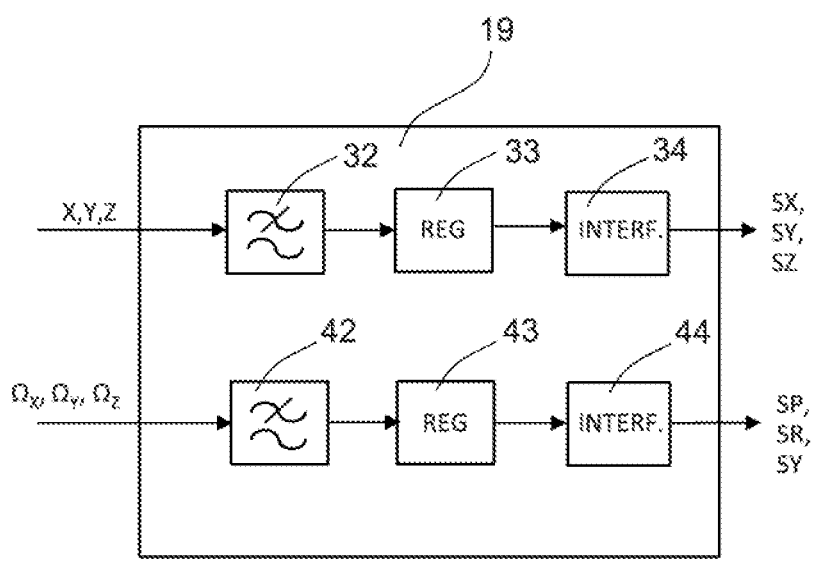
FIG. 10 is a block diagram relating to a filtering module usable in the health state monitoring device of FIG. 6.

The filtering unit 19 may be made as shown by way of example in FIG. 10.

In FIG. 10, each of the displacement signals XL (X, Y, Z) is provided to a first low-pass filter 32; the filtered samples are saved in first registers 33 and output as digital displacement signals SX, SY and SZ through a first interface 34.

Similarly, each of the rotation signals $\Omega$ ($\Omega X$, $\Omega Y$ and $\Omega Z$) is provided to a second low-pass filter 42; the filtered rotation samples are saved in second registers 43 and output as digital rotation signals SP, SR and SY through a second interface 44.

The digital displacement signals SX, SY and SZ and/or the digital rotation signals SP, SR and SY are the filtered movement signals M' (FIG. 6).

With reference again to FIG. 6, the processing unit 18 comprises an ECG parameter calculation unit 25, coupled to the ECG analog-to-digital converter 20; a movement parameter calculation unit 26, coupled to the filtering unit 19; and a decision unit 27, coupled to the parameter calculation units 25, 26. The decision unit 27 is coupled to the output 3 of the monitoring device 1. Each of the "units" described herein may be or include circuitry configured to perform the various functionalities described herein. For example, each of the processing unit 18, ECG parameter calculation unit 25, movement parameter calculation unit 26, and decision unit 17 may be or include circuitry for performing the functionalities of each unit described herein, and in some embodiments, may be integrated within one or more processors or processing circuitry (e.g., may be implemented within the processing unit 18).

Furthermore, the processing unit 18 may comprise a meta-classifier 28, coupled between the output of the decision unit 27 and the output 3 of the monitoring device 1, to filter the results, as explained in detail hereinbelow.

Figure 11:
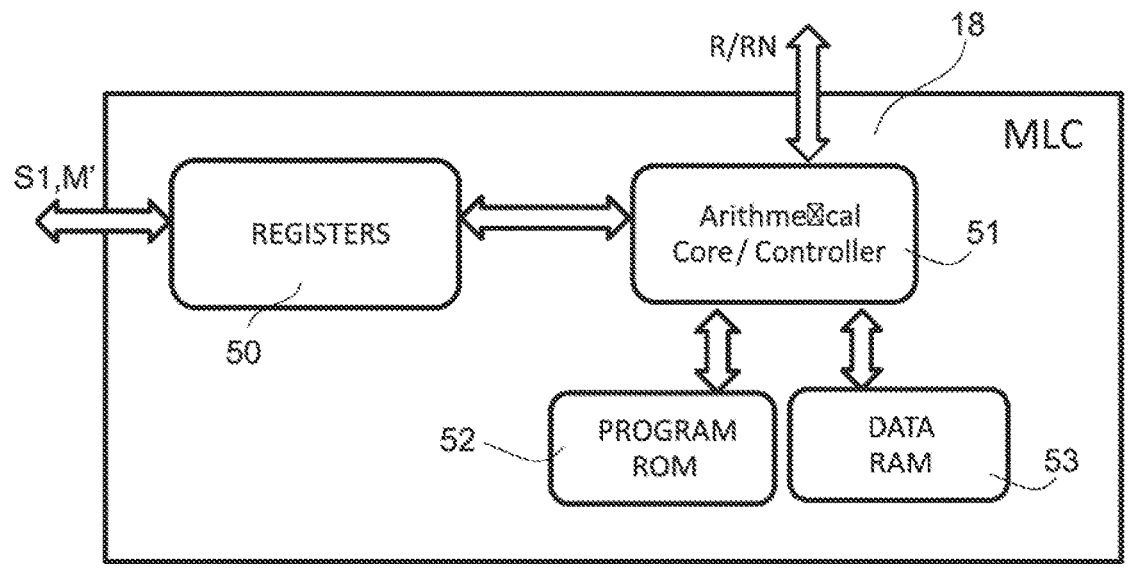
FIG. 11 is a block diagram relating to the hardware structure of a processing unit of the health state monitoring device of FIG. 6.

From the structural point of view, the processing unit 18 is an MLC (Machine Learning Core), having a structure shown in FIG. 11 and described hereinbelow.

In detail, the processing unit 18 comprises one or more registers 50, receiving the ECG signal S1 and the filtered movement signals M' at the input, a calculation unit 51 formed by an arithmetic core or pico-controller and coupled to the registers 50; a program memory 52, for example a ROM (Read Only Memory), coupled to the calculation unit 51; and a data memory 53, for example a RAM (Random Access Memory), also coupled to the calculation unit 51.

With reference again to FIG. 6, the ECG parameter calculation unit 25 has the aim of processing the ECG signal S1 to calculate certain cardiac parameters of interest, used by the decision unit 27 for evaluating the health state. In particular, in the monitoring device 1, the cardiac parameters being monitored are the heart rate HR and the QRS-interval.

To this end, the ECG parameter calculation unit 25 comprises an ECG feature extraction unit 36.

Similarly, the movement parameters calculation unit 26 has the aim of processing the filtered movement signals M' to determine movement parameters or indicators FxR on the basis of features extracted from the filtered movement signals M'. To this end, the movement parameter calculation unit 26 comprises a movement feature extraction unit 37.

In the monitoring device 1, the feature extraction units 36 and 37 are configured to extract the respective features in intervals defined by events detected on the respective signals. In practice, during feature extraction, each event indicates the end of a current evaluation and the beginning of a new evaluation, thereby defining an own moving evaluation window.

Hereinafter, therefore, the events that trigger the extraction of the features are called triggering events and the features being extracted are also called triggered features.

In the embodiment described, as to the ECG signal S1, the triggering events are the detection of peaks of the electrocardiographic signal (and more precisely of the ECG signal S1 thereof) and the triggered features are the duration (time between two triggering events).

Furthermore, the ECG parameter calculation unit 25 might calculate different parameters (such as, for example, the duration of the ECG cycle or the duration of different clinical intervals, such as the PR-interval or PR-segment, or even the height of the waves P, Q, R, S and/or T, see FIG. 2) on the basis of different triggered features.

Figure 12:
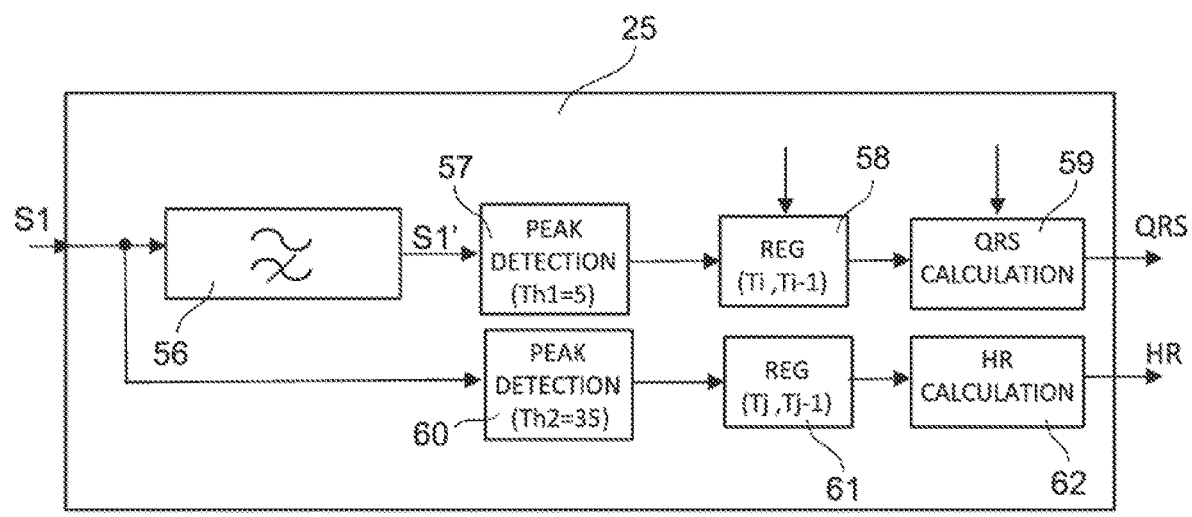
FIG. 12 is a block diagram of an electrocardiographic signal parameter extraction module of the health state monitoring device of FIG. 6.

For example, FIG. 12 shows the structure of a possible logic implementation of the ECG parameter calculation unit 25 for determining the heart rate HR and the QRS-interval.

Figure 4:
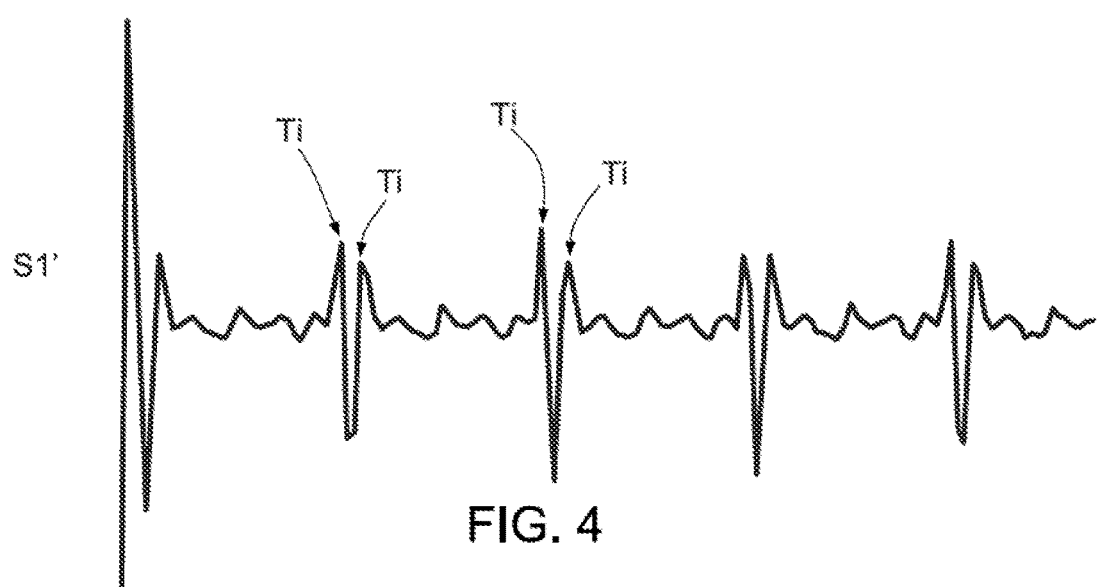
FIG. 4 shows the trend of an electrical signal obtainable by filtering the electrocardiographic signal of FIG. 3.
Figure 5:
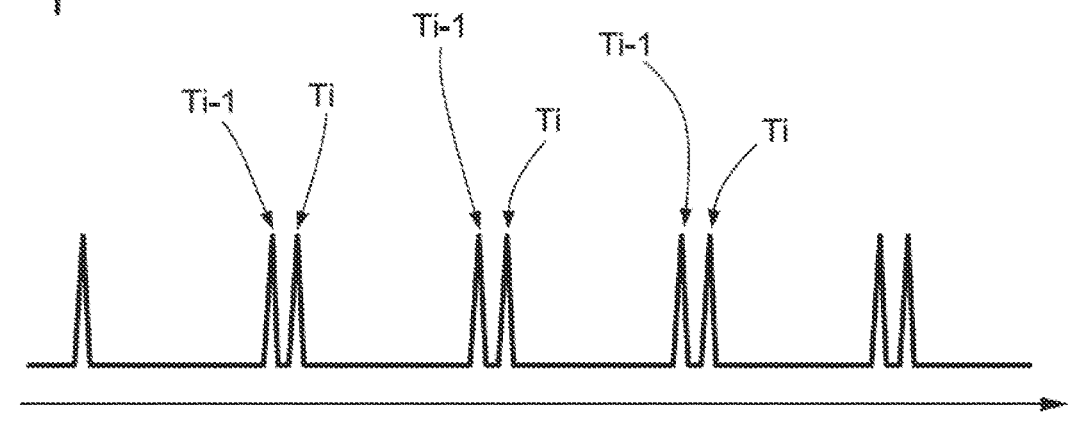
FIG. 5 shows the trend of a signal obtainable by detecting the peaks of the filtered signal of FIG. 4.

The ECG parameter calculation unit 25 of FIG. 12 comprises:
- a high-pass filter 56, configured to receive the ECG signal S1 and output a filtered ECG signal S1' (represented in FIG. 4 as an analog signal, although it is a digital signal, made of a plurality of samples, as indicated above). For example, if the ECG signal S1 is sampled at a frequency of 50 Hz, the high-pass filter 56 may have a cut-off frequency at 3 dB of 10 Hz. As noted, the peaks due to the wave R are no longer present in the filtered ECG signal S1' and the positive peaks being present correspond to the minima of the waves Q and S of the ECG signal (FIG. 2);
- a first peak detection module 57, operating on the basis of a first threshold, Th1, and configured to receive the filtered ECG signal S1' and output information correlated to the time value Ti when each peak occurs, i.e., the instant wherein the filtered ECG signal S1' exceeds the first threshold Th1. The first threshold Th1 is, e.g., 5, correlated to the maximum amplitude of the filtered ECG signal S1' at the waves Q and S of the output voltage Vd' (FIG. 2);
- a first peak register 58, configured to receive the time instants Ti−1 and Ti;
- a QRS-interval calculation module, configured to receive the time instants Ti−1 and Ti and to calculate the distance thereof. The result of this operation is output as a QRS-interval signal;
- a second peak detection module 60, operating on the basis of a second threshold, Th2, and configured to receive the filtered ECG signal S1' and to output information correlated to the time value Tj when each peak occurs, i.e., the instant when the ECG signal S1 exceeds the second threshold Th2. The second threshold Th2 is, e.g., 35, correlated to the maximum amplitude of the ECG signal S1 at the wave R of the output voltage Vd' (FIG. 2);
- a second peak register 61, configured to receive the time instants Tj−1 and Tj; and
- a heart-rate HR calculation module, configured to receive the time instants Tj−1 and Tj and to calculate the difference thereof. The result of this operation is output as heart rate HR.

In particular, the ECG parameter calculation unit 25 may work as described hereinafter with reference to FIG. 13 as to the calculation of the heart rate HR.

Figure 13:
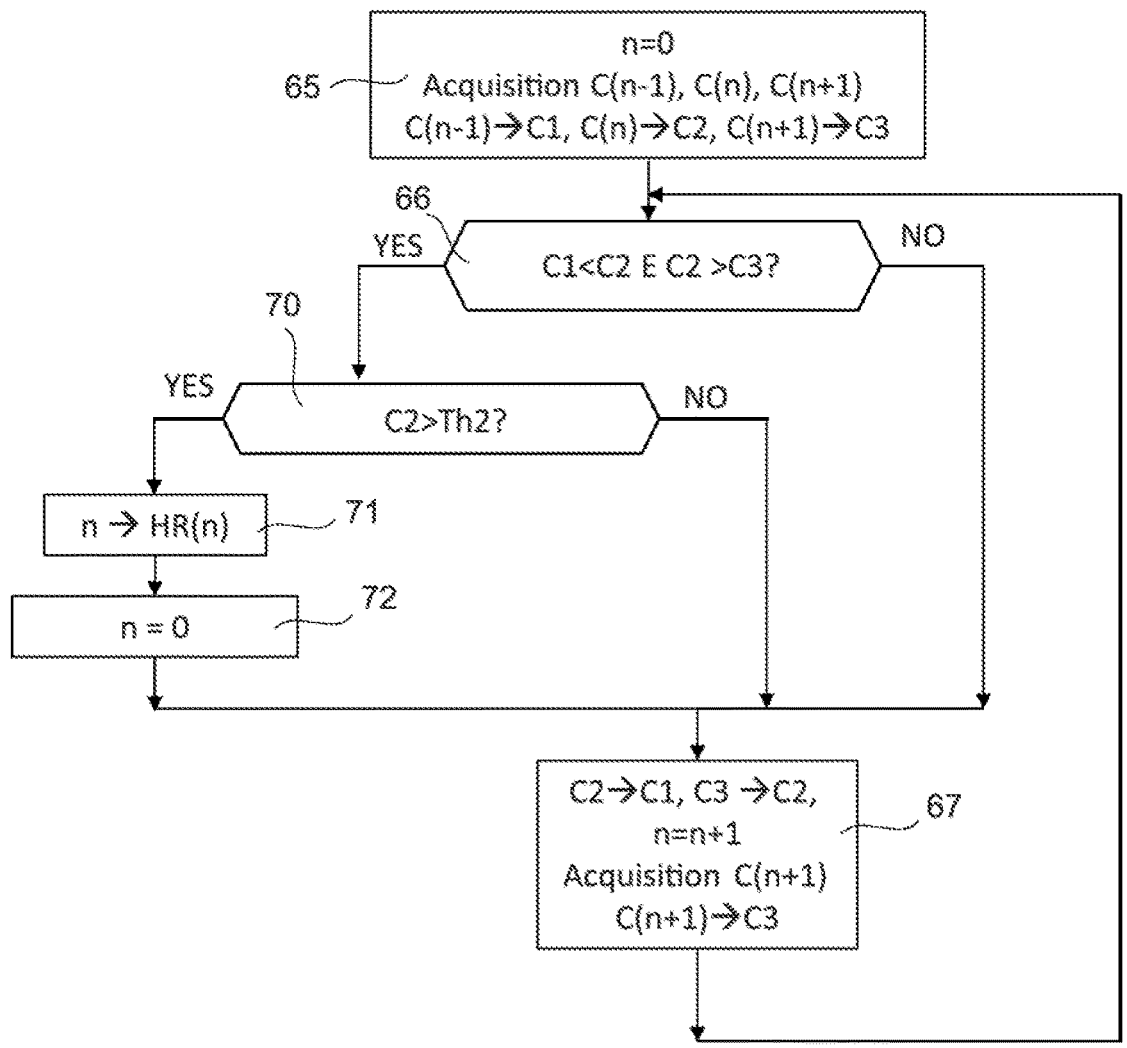
FIG. 13 is a flow chart of operations that may be performed by the electrocardiographic signal parameter extraction module of FIG. 12.

In detail, the HR calculation example shown in FIG. 13 is based on the fact that the samples of the ECG signal S1 (indicated with C(n)) are provided at the sampling frequency, for example every 20 msec, therefore the time distance between two samples may be easily calculated on the basis of the value of a counter being reset when a first peak is recognized and which is increased upon receiving each sample, up to a subsequent sample, when the counter is reset again. In this manner, the count value reached when a peak is recognized corresponds to the time distance, in terms of number of samples, between two peaks.

Figure 14:
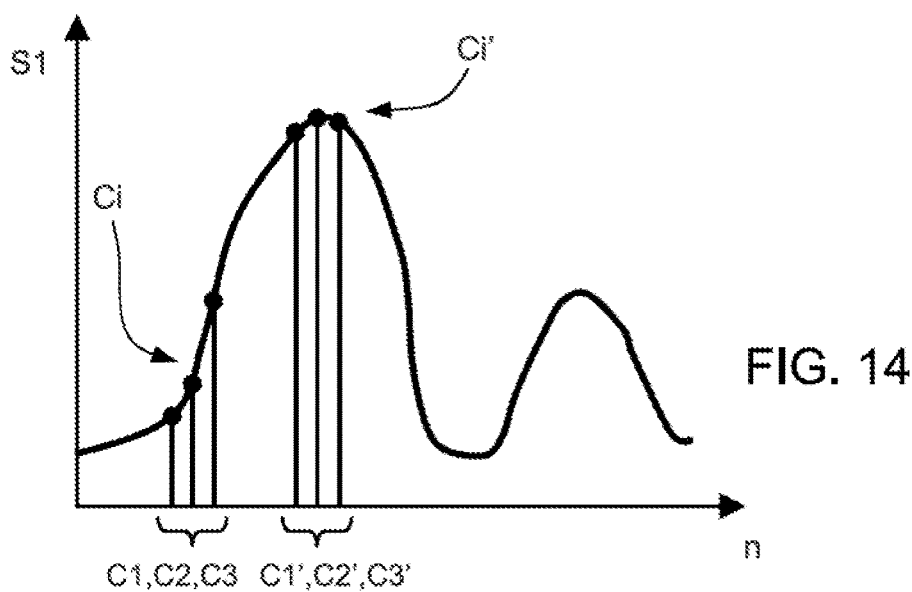
FIG. 14 shows a portion of the electrocardiographic signal of FIG. 3 highlighting samples usable by the electrocardiographic signal parameter extraction module of FIG. 12.

For greater clarity of illustration, reference is also made to FIG. 14, showing a possible trend of a generic portion of the ECG signal S1 made of samples C(n), some of which are shown in FIG. 14.

With initial reference to FIG. 13, in step 65 a counter n is reset (n=0), three samples $C(n-1)$, $C(n)$ and $C(n+1)$ are acquired, and the three samples are stored as saved samples $C1$, $C2$, $C3$.

Then, step 66, the ECG parameter calculation unit 25 verifies the condition (1):

$$C1 < C2 \text{ and } C2 > C3 \qquad (1)$$

that is, verifies whether the intermediate saved sample $C2$ is greater than the previous saved sample $C1$ and the subsequent saved sample $C3$.

In the negative case (as in the case of the group of samples indicated by Ci in FIG. 14), output NO from step 66, the oldest saved sample $C1$ is discarded, the saved samples $C2$ and C3 are renamed C1 and C2; the counter n is increased; a subsequent sample C(n+1) is acquired and saved as C3, step 67.

Saved samples C1-C3 are evaluated again in step 66 to see whether the condition (1) is verified and the verification proceeds with subsequent samples C(i) until condition (1) is verified.

If the condition (1) is verified at step 66 (as occurs, in the example shown in FIG. 14, for the group of samples indicated with Ci'), the output YES is provided from step 66, and the ECG parameter calculation unit 25 verifies whether the saved sample C2 exceeds the second threshold Th2, at step 70.

In the negative (output NO from step 70), the ECG feature extraction unit 36 returns to step 67, for verifying a subsequent triad of samples.

In the positive, output YES from step 70, the counter n already represents the time distance between two peaks (except for the first peak of the signal which will be discussed below); then the ECG feature extraction unit 36 may output this value as a count heart rate HR(n), step 71, and reset counter n, step 72.

Then, the ECG feature extraction unit 36 proceeds again to step 67, for acquiring a subsequent sample and verifying the corresponding triad of samples.

As indicated above, in step 71, at the first identification of a peak in the ECG signal S1, the count value n does not provide a correct heart rate value; in this case, in order to prevent the counter value n from being sent to the output, other steps may be provided, for example using a flag, initially having a value that is modified at the first peak detection, or other solutions obvious to the person skilled in the art, and therefore not described in detail.

The count heart rate value HR(n) thus calculated may be used directly by the decision unit 27 of FIG. 6 to evaluate the health conditions; alternatively, the ECG parameter calculation unit 25 may transform the count heart rate value HR(n) into the heart rate HR through a simple multiplication by the sampling period.

The ECG parameter calculation unit 25 may calculate the QRS-complex in a manner completely similar to what described for the heart rate HR, except for the fact that the peaks are evaluated on the filtered ECG signal S1', rather than on the ECG signal S1, and for the different threshold value used in step 70 (Th1 instead of Th2). In this case, the procedure described in FIG. 13 provides a QRS-complex count value QRS(n) which may be used directly or converted into a time value by the ECG parameter calculation unit 25 or by the decision unit 27 of FIG. 6.

With reference again to FIG. 6, as to each filtered movement signal M', the triggering events are the detection of the positive zero-crossing by the respective filtered movement signal M' (when the filtered movement signal M' crosses the zero and, from negative, becomes positive, or with positive derivative), hereinafter also referred to as positive zero-crossing.

Furthermore, as to each filtered movement signal M', the triggered features may be the peak-to-peak value (amplitude of the signal between a maximum peak and a minimum peak between two triggering events, i.e., between two positive zero-crossings), energy (sum of the square of the amplitudes of the filtered movement signal M' between two triggering events) and duration (time between two triggering events). As explained below, however, a different triggering event, such as the zero-crossing (positive to negative, "negative zero-crossing") and/or different triggered features may be chosen.

In practice, the peak-to-peak value, the energy and the duration represent the movement indicators FxR provided by the movement parameter calculation unit 26 to the decision unit 27.

Figure 15:
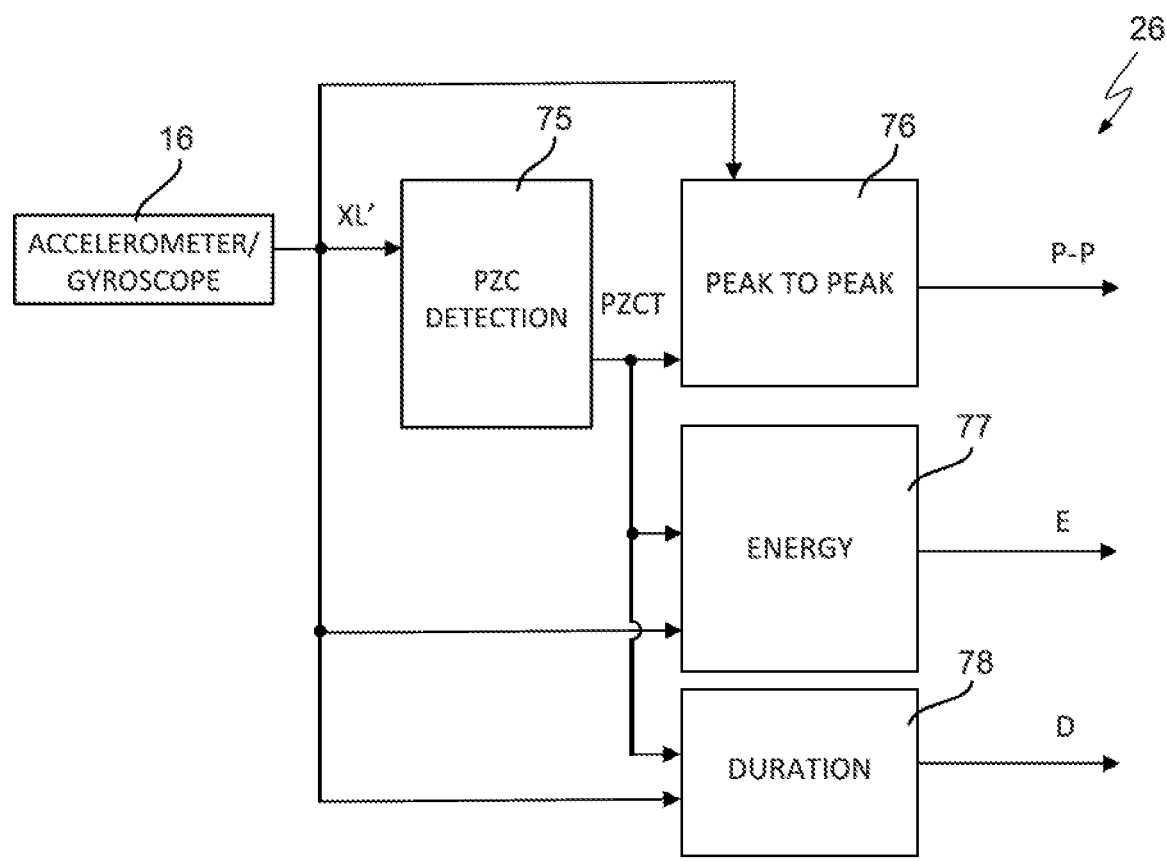
FIG. 15 is a block diagram of a movement signal parameter extraction module usable by the health state monitoring device of FIG. 6.

FIG. 15 shows the structure of a possible logic implementation of the movement parameter calculation unit. In general, the movement parameter calculation unit 26 operates on each of the movement signals M independently of each other, so that the movement parameters FxR are provided in the form of a matrix.

Hereinafter, the description refers to a generic digital displacement signal XL', representative of one of the digital displacement signals SX, SY and SZ and what has been described also applies separately to the other digital displacement signals SX, SY and SZ. Similar processing may also be used for the digital rotation signals SP, SR and SY. In the described embodiment, the movement feature extraction unit 26 detects the zero-crossing of the digital displacement signal XL' with positive derivative, as a triggering event, and calculates at least one feature selected among energy, peak-to-peak value and duration as a triggered feature.

In detail, the movement feature extraction unit 26 of FIG. 15 comprises:

a positive zero-crossing detection module 75, configured to receive the digital displacement signal XL' and output a positive zero-crossing signal PZCT. This signal is conceptually composed by a plurality of pulses, one at each detection of a zero-crossing (negative to positive) of the digital displacement signal XL';

a peak-to-peak range determination module 76, configured to receive the digital displacement signal XL' and the positive zero signal PZCT and generate a peak-to-peak signal P-P, as the amplitude difference between the maximum value and the minimum value of the digital displacement signal XL' in the time interval comprised between two subsequent triggering pulses of the positive zero signal PZCT;

an energy determination module 77, configured to receive the digital displacement signal XL' and the positive zero signal PZCT and generate an energy signal E as the sum of the square values of the digital displacement signal XL' in a predetermined time interval (for example 2 sec, from a triggering pulse of the positive zero signal PZCT); and a duration determination module 68, configured to receive the digital displacement signal XL' and the positive zero signal PZCT and generate a duration signal D as the time distance between two subsequent pulses of the positive zero signal PZCT.

The signals P-P, E, D and possibly PZCT are the matrix of movement parameters FxR supplied to the decision unit 27.

In a manner not shown, as indicated, the movement feature extraction unit 26 may comprise similar modules for evaluating the peak-to-peak value, the energy and the duration of the rotation signals Ω.

With reference again to FIG. 6, the ECG HR, QRS parameters and the movement parameters FxR are used by the decision unit 27 to evaluate the health state.

In particular, the decision unit 27 may be a plurality of decision trees, one for each group of features.

For example, the decision unit 27 may comprise a tree configured to first evaluate the matrix of movement parameters FxR to determine whether the person is stationary (and therefore the measurements are reliable) or not. If a movement situation is detected, the decision unit 27 may output a movement signal, e.g., a 0, for example to the external processor 14 (FIG. 6), and stop.

The evaluation of the displacement parameters P-P, E and D may be performed in a known manner, for example simply by evaluating whether all the movement parameters are lower than respective predetermined thresholds; alternatively, the decision unit 27 may comprise a processing unit which calculates a single cumulative parameter K and compares it with a single threshold. For example, in the code of FIG. 16, the threshold of the cumulative parameter K is set equal to 1.2 g). Alternatively, other criteria may be used, see for example: "Human motion detection in daily activity tasks using wearable sensors," O. Politi, I. Mporas, V. Megalooikonomou, published in "2014 22nd European Signal Processing Conference (EUSIPCO)", pp. 2315-2319, ISBN: 978-0-9928-6261-9 or "Convolutional neural networks for human activity recognition using multiple accelerometer and gyroscope sensors," Ha, S.; Choi, S., Proceedings of the 2016 International Joint Conference on Neural Networks (IJCNN), Vancouver, BC, Canada, Jul. 24-29, 2016; pp. 381-388.

If, on the other hand, a rest situation is detected, the decision unit 27 may proceed to evaluate the health state on the basis of the ECG features (HR, QRS-complex, in the embodiment shown) and to output a signal STATUS whose value is indicative of the health state.

The health state may for example be evaluated by comparing the heart rate HR and the QRS-complex with respective low and high thresholds: typically, and in accordance with the usual medical practice, there are identified a normal condition if the heart rate is comprised between 60 and 100 beats/minute, a bradycardia condition if the heart rate is less than 60 beats/minute, and a tachycardia condition if the heart rate is above 100 beats/minute; the QRS-complex is instead considered normal if comprised between 80 and 120 msec.

In particular, the decision unit 27 may output a two-variable signal, based on the identified condition. For example, the output signal may have value B, N, or T (brachycardia, normal, or tachycardia), as to the heart rate, and Q-N, Q-CL, or QA (normal, control value, or abnormal) as to the QRS-complex, for example according to what shown in detail in FIG. 16.

The output signal STATUS may therefore assume nine different values.

According to a variant of the decision process implemented by the decision unit 27, the latter may also provide a reliability verification of the received values of the heart rate HR and/or of the QRS-complex. For example, in order to discard QRS-complex values calculated on adjacent cardiac cycles (i.e., the distance between the wave S of one cycle and the wave Q of the subsequent cardiac cycle), the decision unit 27 may provide, after the verification on the movement state |K|>1.2 g, a verification on the QRS value, to discard values being greater than a threshold (for example greater than 300 msec).

With reference again to FIG. 6, in case the meta-classifier 28 is coupled between the output of the decision unit 27 and the output 3 of the monitoring device 1, a stabilization of the results may be performed.

In particular, the meta-classifier 28 may be substantially formed by a plurality of counters associated with respective comparison elements. In particular, for each possible value of the output signal STATUS of the decision unit 27 (i.e., for each of the nine values of the output signal STATUS B_Q-N, B_Q-A, etc.), the meta-classifier 28 may comprise a counter which is increased when the output variable has the associated value and is decreased, when the output variable has a value different from the associated one.

The meta-classifier 28 outputs the counter value which reaches a maximum value and modifies its output only when the output of the decision unit 27 changes for a predetermined number of times.

The following table shows a possible operating criterion of the meta-classifier 28 in the simplified situation wherein the output of the decision unit 27 may assume only a first value A and a second value B, and wherein the switching threshold (maximum count value of the respective counters) is equal to 4:

TABLE 1

| Decision tree result | A | A | A | B | A | B | B | B | A | B | B | B | A | A | A |
|---|---|---|---|---|---|---|---|---|---|---|---|---|---|---|---|
| Counter A (End counter = 3) | 1 | 2 | 3 | 2 | 3 | 2 | 1 | 0 | 1 | 0 | 0 | 0 | 1 | 2 | 3 |
| Counter B (End counter = 4) | 0 | 0 | 0 | 1 | 0 | 1 | 2 | 3 | 2 | 3 | 4 | 5 | 4 | 3 | 2 |
| Machine Learning Core result (including meta-classifier) | x | x | A | A | A | A | A | A | A | A | B | B | B | B | A |

As is noted, in the simplified situation shown, the meta-classifier 28 outputs the first value A until the counter of the second value B reaches the value 4.

In practice, the meta-classifier 28 contributes to reducing the number of false positives, avoiding outputting unstable values and reducing the transitions of the monitoring device 1.

The monitoring device 1 is therefore able to detect the health state on the basis of simple calculations, without needing high processing capacity or memory capacity, since it does not need to store a large number of samples or associated variables.

In fact, the evaluation of cardiac and movement parameters in a triggered manner allows identification of a very small number of time instants, linked to the monitored event, which may be processed, through particularly simple mathematical operations, by functional units which are in turn very simple, and temporarily stored in small memory elements.

This causes the monitoring device 1 to have very small dimensions and require or otherwise should have low operating power. It may thus be inserted in a single package to form a single chip and may thus be embedded in a low-power portable device, while still providing reliable results.

For example, the implementation of the monitoring device 1 may provide for the use of a pico-controller with a group of instructions dedicated to the application, which leads to a silicon area occupation of about 7K gates (7 thousand logic gates) and therefore with a considerable area advantage with respect to the use of a general-purpose microcontroller which, in the smallest version currently available on the market, has an area occupation of 25K gates.

Furthermore, the monitoring device 1 may be incorporated in a personal computer, as described above with reference to FIG. 8. In this case, with suitable calibration, placing a finger of one hand on the pad 12A and a finger of the other hand on the pad 12B of the personal computer 200, the ECG detector 15 may acquire the voltage Vd between the fingers, allowing the acquisition of the cardiac parameters HR, QRS; the movement signal in this case allows verifying whether the personal computer 200 is stationary or moving.

Figure 17:
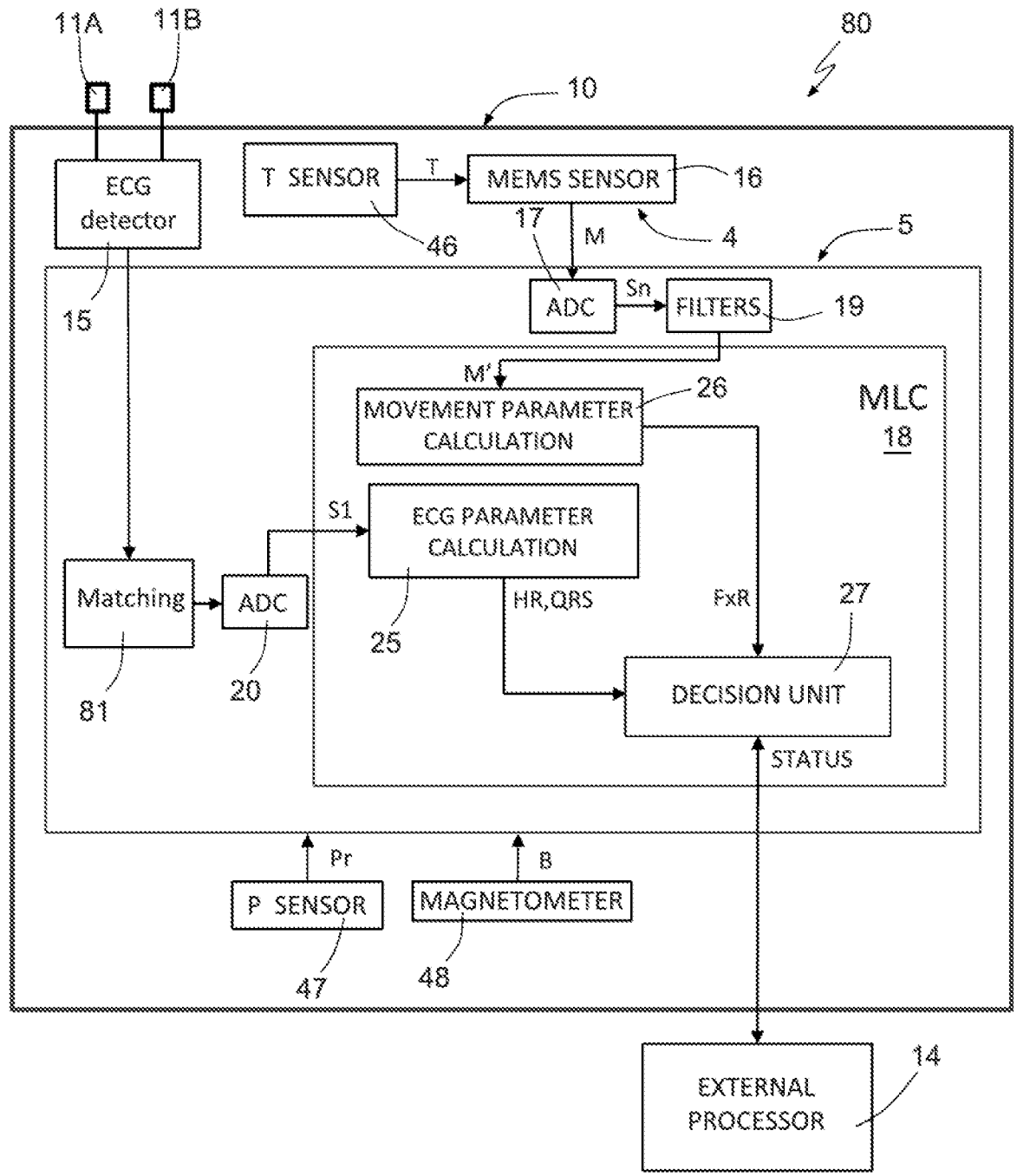
FIG. 17 is a block diagram of another embodiment of the present health state monitoring device.

FIG. 17 shows a different embodiment of the monitoring device, indicated here with 80. In FIG. 17, parts which are the same of the monitoring device 1 of FIG. 6 are indicated by the same reference numbers and will not be described.

In detail, in the monitoring device 80, the ECG detector 15 is external to the second die 5 and a matching network 81 is arranged between the ECG detector 15 and the ECG analog-to-digital converter 20.

Furthermore, the monitoring device 80 of FIG. 17 is further coupled to a plurality of additional sensors, such as a temperature sensor 46, a pressure sensor 47 and a magnetometer 48, useful to reduce the influences of the external environment on the measures of the acquired signals.

In particular, the temperature sensor 46 may provide a temperature signal T usable by the MEMS sensor 16, and in particular by the associated amplification circuits, to modify the amplification level on the basis of the temperature, in a per se known manner.

Similarly, the pressure sensor 47 and the magnetometer 48 are useful to provide a pressure signal Pr and a magnetic field signal B (for example, in the absence of other sources, the earth magnetic field), respectively.

For example, the pressure signal Pr may be used by the decision unit 27 to evaluate whether the patient is moving, since pressure is a function of altitude. In this case, in particular, the pressure signal Pr may be used to understand whether the patient is going up or down the stairs in a building and trigger the measurement immediately after this identification and/or may carry out more complex verifications, as indicated below.

Alternatively, the pressure signal Pr may be used to enable the monitoring device 80 to measure the health state at high altitude.

The magnetic field signal B may be used to give an indication of the direction of movement, as described for example in the article "Human Activity Recognition Using Inertial/Magnetic Sensor Units" by Kerem Altun, B. Barshan, DOI:10.1007/978-3-642-14715-9_5, Corpus ID: 8728793; published in HBU 2010, Engineering, Computer Science.

In should be noted that the temperature sensors 46, the pressure sensor 47 and the magnetometer 48 might be, at least in part, integrated into the chip 10.

In a manner not shown, a meta-classifier, similar to the meta-classifier 28 of FIG. 6, might be present.

Figure 18:
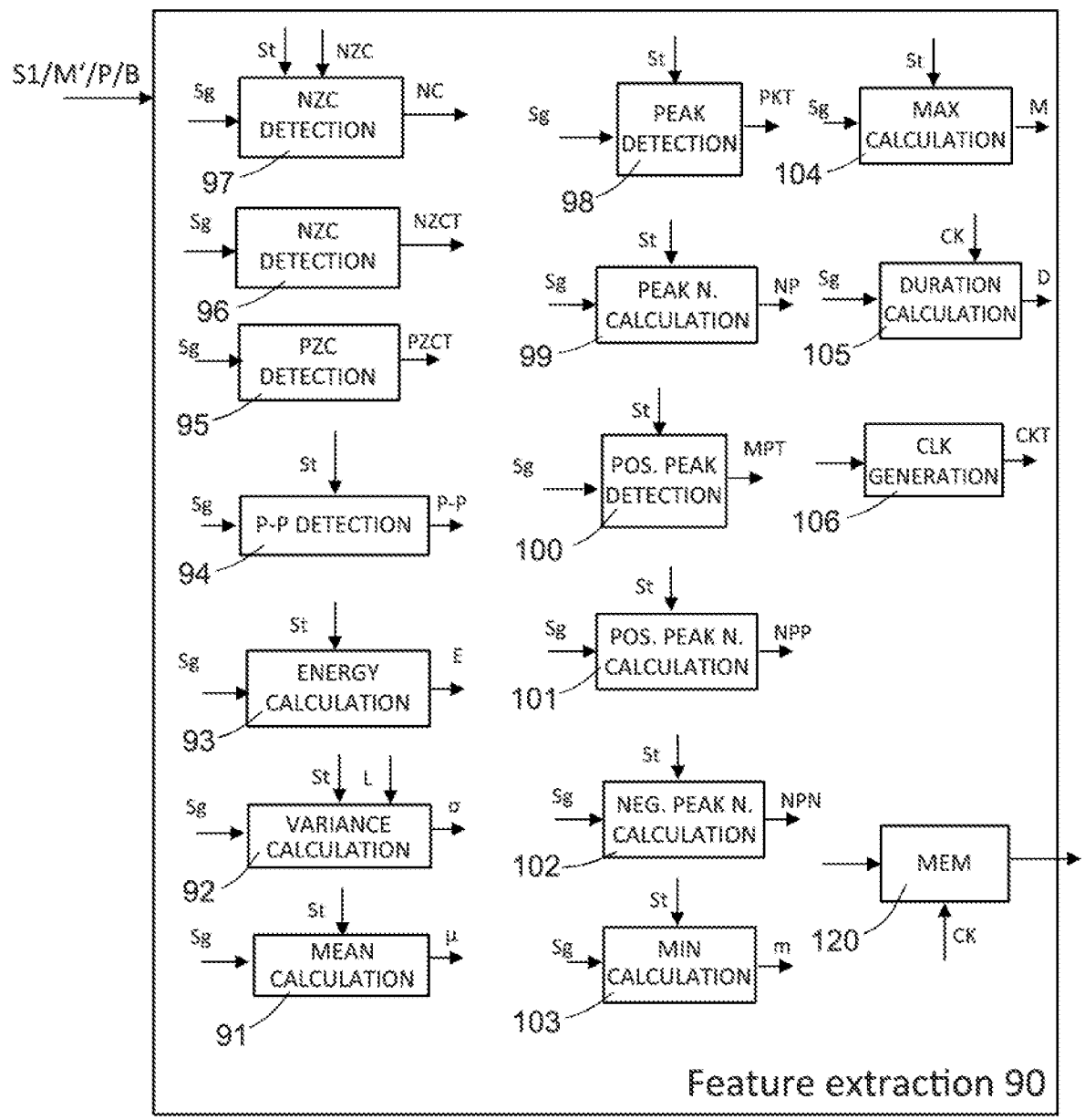
FIG. 18 is a block diagram of a generic parameter extraction module usable in the health state monitoring device of FIG. 6 or FIG. 17.

FIG. 18 shows a diagram of a different embodiment of a feature extraction unit, indicated with 90.

The feature extraction unit 90 comprises a plurality of feature extraction modules, some intended to determine triggering events, others intended to determine triggered features, as explained in detail hereinbelow.

The feature extraction unit 90 is configured to operate on the ECG signal S1, on one or more of the filtered movement signals M' and/or on a generic signal, such as the pressure signal Pr, the terrestrial magnetic field signal B and the temperature signal T of the monitoring device 80 of FIG. 17.

In FIG. 18, the input signal whose features are desired to be extracted is therefore generically indicated with Sg.

Furthermore, since the detection of certain features may be triggered by different triggering events, in this case the generic triggering event is generically indicated with St.

In detail, the feature extraction unit 90 comprises one or more of the following modules:

a mean calculation module 91, configured to calculate the mean of the value of the input signal Sg between two triggering events St. This module outputs a mean value μ which may be saved in a cell of a buffer unit 120, for example a RAM;

a variance calculation module 92, configured to calculate the variance of the input signal Sg between two triggering events St, according to the equation:

$$\sigma = \left[\left(\frac{\sum_D Sg^2}{D}\right) - \left(\frac{\sum_D Sg}{D}\right)^2\right]$$

wherein D is the duration of the evaluation window (time distance between the two triggering events St), provided by a specific module, as described below. This module outputs a variance value σ which may be saved in two cells of the buffer unit 120;

an energy calculation module 93, configured to calculate the energy of the input signal Sg within a window delimited between two triggering events St (or of predetermined duration from a triggering event St); the energy is defined as the sum of the squares of the values of the input signal Sg inside the window. This module outputs an energy value E which may be saved in a cell of the buffer unit 120;

a peak-to-peak value calculation module 94, configured to calculate the difference between the maximum value and the minimum value of the input signal Sg between two triggering events St. This module outputs a peak-to-peak value P-P which may be saved in a cell of the buffer unit 120;

a positive zero-crossing detection module 95, configured to detect when the input signal Sg becomes positive from negative. This signal is a triggering event, indicated with PZRT, and is provided to other modules, when provided;

a negative zero-crossing detection module 96, configured to detect when the input signal Sg becomes negative from positive. This signal is a triggering event, indicated with NZRT, and is provided to other modules, when provided;

a negative zero-crossing number calculation module 97, configured to calculate the number of negative crossings, for example in a specific time interval from the reception of a triggering event St. This module outputs the number of negative crossings, called negative count value NC, which may be saved in a cell of the buffer unit 120;

a peak detection module 98, configured to detect when the input signal Sg assumes a maximum or minimum value. This signal is a triggering event, indicated with PKT, and is provided to other modules, when provided;

a peak calculation module 99, configured to calculate the peak number of the input signal Sg between two triggering events St. This module outputs a peak number NP that may be saved in cells of the buffer unit 120;

a positive peak detection module 100, configured to detect when the input signal Sg assumes its maximum value.

This signal is a triggering event, indicated with MPT, and is provided to other modules, when provided;

a positive peak calculation module 101, configured to calculate the positive peak number of the input signal Sg between two triggering events St. This module outputs a positive peak number NPP that may be saved in cells of the buffer unit 120;

a negative peak calculation module 102, configured to calculate the negative peak number of the input signal Sg between two triggering events St. This module outputs a negative peak number NPN that may be saved in cells of the buffer unit 120;

a minimum detection module 103, configured to detect the minimum value of the input signal Sg between two triggering events St. This module outputs a minimum value m which may be saved in cells of the buffer unit 120;

a maximum detection module 104, configured to detect the maximum value of the input signal Sg between two triggering events St. This module outputs a maximum value M which may be saved in cells of the buffer unit 120;

a duration calculation module 105, configured to calculate the duration (as a number of clock pulses provided by the clock circuit 29 or as a number of samples of the input signal Sg) between two triggering events St; and a clock generation module 106, configured to generate a triggering event CKT, usable by other feature generation modules or by the decision unit 27 (FIG. 6 or 17).

By using some of the modules 91-106 described above, the monitoring device may be configured for calculating other cardiac parameters of a patient, including (see FIG. 2): the amplitude of the wave P; the amplitude of the wave R; the amplitude of the wave Q; the amplitude of the wave T; the PQ-interval or the PR-interval, having normal reference values existing therefor (see for example Table 1 of the article: "QRS Detection and Heart Rate Variability Analysis: A Survey," Rami J. Oweis, Basim O. Al-Tabbaa, Biomedical Science and Engineering, 2014, Vol. 2, No. 1, 13-34, DOI: 10.12691/bse-2-1-3.

The monitoring device described herein has numerous advantages.

In particular, it allows the integration of health state evaluation functions in dice/chips arranged in a single package, with reduced consumption. In this manner, the device has small size and long duration (autonomy); it may be made as a stand-alone apparatus or may be used in small size, portable electronic apparatuses, for example it may be associated with a personal computer, as discussed above.

It allows artifacts of the acquired cardiac signal to be removed or at least considerably reduced, even with a simple and small-size structure.

Finally, it is clear that modifications and variations may be made to the monitoring device and method described and illustrated herein without thereby departing from the scope of the present disclosure, as defined by the attached claims. For example, the different described embodiments may be combined to provide further solutions.

Some functions, described herein in analogue terms, might be implemented by corresponding digital components, and vice versa.

The evaluation of the movement/rest state may include complex situations, such as:

1. evaluation of the activity performed by a patient on the basis of the movement signals XL, with measurement carried out during or after a specific movement (if it does not generate artifacts); and 2. evaluation of the rotation signals provided by the integrated gyroscope by a further decision unit for the identification of the activity in progress and measurement during or after a specific movement.

Furthermore, although the described monitoring device is based on the determination of cardiac parameters detected in moving windows determined by the triggering events, auxiliary units for cardiac parameter determination operating on fixed time windows may be provided. In this case, the units for cardiac parameter determination on moving and fixed windows may be enabled alternatively, for example through an external command, or be active in parallel. In this second case, the decision unit 27 may provide comparing the parameters, discarding the results in case they have very different values.

The obtained parameters may be provided directly to the outside for more sophisticated processing. In this case, the processing unit 18 may be absent.

A device (1; 80) of monitoring the health state, may be summarized as including a semiconductor die (5) integrating an electric potential sensor (15), configured to detect potential variations present on the body of a living being and associated with a heart rhythm and to generate a cardiac signal (S1); and a cardiac parameter determination unit (25), configured to receive the cardiac signal and determine cardiac parameters indicative of a health state, wherein the cardiac parameter determination unit is configured to detect triggering events and to determine features of the cardiac signal in time windows defined by the triggering events.

The health monitoring device may further include a decision unit (18), configured to receive cardiac parameters and generate a health signal based on a comparison with threshold values.

The cardiac parameters may include heart rate and QRS-complex.

The triggering events may include threshold exceeding and the cardiac parameter determination unit (25) may include a module (59, 62) for detecting the time distance between two triggering events exceeding the thresholds.

The cardiac parameter determination unit (25) may include a heart rate detection unit (60-62, 65-72), the heart rate detection unit being configured to: a) initialize (65) a first counter configured to provide a count value; b) receive (65) a sample (C(n)) of the cardiac signal (S1), the sample having a value; c) verify (66) whether the sample value is a peak value; d) increase (67) the first counter and repeat steps b) and c) if the verification c) gives a negative result; e) verify (70) whether the sample value exceeds a heart rate threshold if the verification c) gives a positive result; f) acquire (71) the count value of the first counter as heart rate information if the verification e) gives a positive result; g) increase (67) the first counter and repeat steps b)-e) if the verification e) gives a negative result.

The cardiac parameter determination unit (25) may further include a QRS-complex detection unit (56-59, 65-72), the QRS-complex detection unit being configured to: a) receive the cardiac signal (S1); b) filter (56) the cardiac signal through a high-pass filter to obtain a filtered signal (S1'); c) initiate (65) a second counter configured to provide a count value; d) acquire (65) a sample (C(n)) of the filtered signal having a value; e) verify (66) whether the sample value of the filtered signal is a peak value; f) increase (67) the second counter and repeat steps d)-e) if the verification 1) gives a negative result; g) verify (70) whether the sample value of the filtered signal exceeds a QRS threshold if the verification e) gives a positive result; h) acquire (71) the count value of the second counter as heart rate information if the verification n) gives a positive result; i) increase (67) the second counter and repeat steps d)-g) if the verification e) gives a negative result.

Initiating (65) may include resetting the count value.

The health monitoring device may further include a MEMS movement sensor (16) and a movement parameter determination unit (26) coupled to the MEMS sensor and to the decision unit (18), wherein the MEMS movement sensor (15) may be configured to generate an inertial signal; the movement parameter determination unit (26) may be configured to detect movement parameters of the inertial signal; and the decision unit (18) may be configured to receive the movement parameters, detect a movement condition or a rest condition from the movement parameters and generate a movement signal in response to detection of the movement condition and provide a health state information on the basis of cardiac parameters in response to detecting the rest condition.

The MEMS movement sensor (15) may be an accelerometer and/or a gyroscope and may be integrated in a further die (4) coupled to the semiconductor material die (5).

The cardiac parameter determination unit (25) and the decision unit (18) may include a machine learning core.

The machine learning core (18) may be configured to receive an input signal (Sg) and may include at least one of the following triggering event detection modules: a) a positive zero-crossing detection module (95), configured to detect when the input signal goes from negative to positive; b) a negative zero-crossing detection module (96), configured to detect when the input signal goes from positive to negative; c) a peak detection module (98), configured to detect when the input signal assumes a maximum or minimum value; d) a positive peak detection module (100), configured to detect when the input signal assumes a maximum value; and e) a clock generation module (106), configured to generate a clock event (CKT), and at least one of the following triggered feature detection modules: f) a mean calculation module (91), configured to calculate a mean of values of the input signal in a window delimited between two triggering events; g) a variance calculation module (92), configured to calculate a variance of the input signal between two triggering events; h) an energy calculation module 93, configured to calculate an energy of the input signal within a window delimited between two triggering events or a window of predetermined duration from a triggering event; i) a peak-to-peak value calculation module (94), configured to calculate the difference between a maximum value and a minimum value of the input signal in a window delimited between two triggering events or in a window of predetermined duration from a triggering event; j) a negative zero-crossing number calculation module (97), configured to calculate a number of negative crossings in a window delimited between two triggering events or in a window of predetermined duration from a triggering event; k) a peak calculation module (99), configured to calculate a peak number of the input signal in a window delimited between two triggering events St; l) a positive peak calculation module (101), configured to calculate a positive peak number of the input signal in a window delimited between two triggering events; m) a negative peak calculation module (102), configured to calculate a negative peak number of the input signal in a window delimited between two triggering events; n) a minimum detection module (103), configured to detect a minimum value of the input signal in a window delimited between two triggering events; o) a maximum detection module (104), configured to detect a maximum value of the input signal in a window delimited between two triggering events; and p) a duration calculation module (105), configured to calculate a duration of the input signal in a window delimited between two triggering events.

An electronic apparatus may be summarized as including the health monitoring device (1; 80), and may include electrodes (8A, 8B) for detecting the cardiac signal.

The electronic apparatus may include a personal computer (200) including a first and a second key (12A, 12B) forming the electrodes for detecting the cardiac signal.

A method of monitoring health using a health monitoring device integrated into a semiconductor material die, the method may be summarized as including detecting electric potential variations on the body of a living being and associated with a heart rhythm; generating a cardiac signal; determining cardiac parameters indicative of a health state on the basis of the cardiac signal; wherein determining cardiac parameters comprises detecting triggering events and detecting features of the cardiac signal in time windows defined by the triggering events.

The health monitoring method may further include receiving cardiac parameters and generating a health signal based on a comparison with threshold values.

Generating a cardiac signal may include generating a digital signal including a sequence of samples and detecting cardiac parameters comprises detecting the heart rate, wherein detecting the heart rate comprises: receiving the samples of the cardiac signal; detecting a first exceeding of a first threshold of the cardiac signal by a first peak sample of the sequence of samples; initiating a first counter upon detecting the first exceeding; incrementing the counter upon receiving samples subsequent to the first peak sample; detecting a second exceeding of the first threshold of the cardiac signal by a second peak sample of the sequence of samples; acquiring a count value of the first counter upon detecting the second exceeding.

The health monitoring method may include generating an inertial signal through a MEMS movement sensor; detecting movement parameters of the inertial signal; and detecting a movement condition or a rest condition from the movement parameters; generating a movement signal in response to detection of the movement condition; and providing a health state information based on the cardiac parameters in response to detection of the rest condition.

The health monitoring method may include receiving an input signal (Sg); detecting at least one of the following triggering events of the input signal: a) detecting when the input signal goes from negative to positive and generating a positive zero-crossing event; b) detecting when the input signal goes from positive to negative and generating a negative zero-crossing event; c) detecting when the input signal assumes a maximum or minimum value and generating a peak event; d) detecting when the input signal assumes a maximum value and generating a maximum event; and e) generating a clock event CKT, and detecting at least one of the following features of the input signal: f) calculating the mean of values of the input signal in a window delimited between two triggering events St; g) calculating the variance of the input signal between two triggering events; h) calculating the energy of the input signal within a window delimited between two triggering events or a window of predetermined duration from a triggering event; i) calculating the difference between the maximum value and the minimum value of the input signal in a window delimited between two triggering events or in a window of predetermined duration from a triggering event; j) calculating the number of negative crossings in a window delimited between two triggering events or in a window of predetermined duration from a triggering event; k) calculating the peak number of the input signal in a window delimited between two triggering events; l) calculating the positive peak number of the input signal in a window delimited between two triggering events; m) calculating the negative peak number of the input signal in a window delimited between two triggering events St; n) detecting the minimum value of the input signal in a window delimited between two triggering events; o) detecting the maximum value of the input signal in a window delimited between two triggering events; calculating the duration of the input signal in a window delimited between two triggering events.

The various embodiments described above can be combined to provide further embodiments. These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A device of monitoring the health state, comprising:
a semiconductor die, including:
an electric potential sensor configured to detect potential variations present on a body of a living being and associated with a heart rhythm and to generate a cardiac signal; and
cardiac parameter determination circuitry configured to receive the cardiac signal and determine cardiac parameters indicative of a health state,
wherein the cardiac parameter determination circuitry is configured to detect triggering events and to determine features of the cardiac signal in time windows defined by the triggering events;
one or more electrodes electrically coupled to the electric potential center; and
a personal computer, wherein the one or more electrodes include a first and second key of the personal computer.

2. The health monitoring device according to claim 1, further comprising decision circuitry configured to receive the cardiac parameters and generate a health signal based on a comparison with threshold values.

3. The health monitoring device according to claim 1, wherein the cardiac parameters include heart rate and QRS-complex.

4. The health monitoring device according to claim 1, wherein the triggering events include threshold exceeding and the cardiac parameter determination circuitry is configured to detect a time distance between two triggering events exceeding the thresholds.

5. The health monitoring device according to claim 1, wherein the cardiac parameter determination unit includes heart rate detection circuitry, the heart rate detection circuitry being configured to:
a) initialize a first counter configured to provide a count value;
b) receive a sample of the cardiac signal, the sample having a value;
c) verify whether the sample value is a peak value;
d) increase the first counter and repeat steps b) and c) if the verification c) gives a negative result;
e) verify whether the sample value exceeds a heart rate threshold if the verification c) gives a positive result;
f) acquire the count value of the first counter as heart rate information if the verification e) gives a positive result;

g) increase the first counter and repeat steps b)-e) if the verification e) gives a negative result.

6. The health monitoring device according to claim 5, wherein the cardiac parameter determination unit further comprises QRS-complex detection circuitry, the QRS-complex detection circuitry being configured to:
h) receive the cardiac signal;
i) filter the cardiac signal through a high-pass filter to obtain a filtered signal;
j) initiate a second counter configured to provide a count value;
k) acquire a sample of the filtered signal having a value;
l) verify whether the sample value of the filtered signal is a peak value;
m) increase the second counter and repeat steps k)-l) if the verification l) gives a negative result;
n) verify whether the sample value of the filtered signal exceeds a QRS threshold if the verification l) gives a positive result;
o) acquire the count value of the second counter as heart rate information if the verification n) gives a positive result;
p) increase the second counter and repeat steps k)-n) if the verification e) gives a negative result.

7. The health monitoring device according to claim 5, wherein initiating includes resetting the count value.

8. The health monitoring device according to claim 2, further comprising a MEMS movement sensor and movement parameter determination circuitry coupled to the MEMS sensor and to the decision circuitry,
wherein the MEMS movement sensor is configured to generate an inertial signal;
the movement parameter determination circuitry is configured to detect movement parameters of the inertial signal; and
the decision circuitry is configured to receive the movement parameters, detect a movement condition or a rest condition from the movement parameters and generate a movement signal in response to detection of the movement condition and provide a health state information on the basis of cardiac parameters in response to detecting the rest condition.

9. The health monitoring device according to claim 8, wherein the MEMS movement sensor is an accelerometer or a gyroscope and is integrated in a further die coupled to the semiconductor material die.

10. The health monitoring device according to claim 2, wherein the cardiac parameter determination circuitry and the decision circuitry include a machine learning core.

11. The health monitoring device according to claim 10, wherein the machine learning core is configured to receive an input signal and includes at least one of:
a) a positive zero-crossing detection module, configured to detect when the input signal goes from negative to positive;
b) a negative zero-crossing detection module, configured to detect when the input signal goes from positive to negative;
c) a peak detection module, configured to detect when the input signal assumes a maximum or minimum value;
d) a positive peak detection module, configured to detect when the input signal assumes a maximum value; or
e) a clock generation module, configured to generate a clock event,
and at least one of the following triggered feature detection modules:

f) a mean calculation module, configured to calculate a mean of values of the input signal in a window delimited between two triggering events;
g) a variance calculation module, configured to calculate a variance of the input signal between two triggering events;
h) an energy calculation module, configured to calculate an energy of the input signal within a window delimited between two triggering events or a window of predetermined duration from a triggering event;
i) a peak-to-peak value calculation module, configured to calculate the difference between a maximum value and a minimum value of the input signal in a window delimited between two triggering events or in a window of predetermined duration from a triggering event;
j) a negative zero-crossing number calculation module, configured to calculate a number of negative crossings in a window delimited between two triggering events or in a window of predetermined duration from a triggering event;
k) a peak calculation module, configured to calculate a peak number of the input signal in a window delimited between two triggering events;
l) a positive peak calculation module, configured to calculate a positive peak number of the input signal in a window delimited between two triggering events;
m) a negative peak calculation module, configured to calculate a negative peak number of the input signal in a window delimited between two triggering events;
n) a minimum detection module, configured to detect a minimum value of the input signal in a window delimited between two triggering events;
o) a maximum detection module, configured to detect a maximum value of the input signal in a window delimited between two triggering events; or
p) a duration calculation module, configured to calculate a duration of the input signal in a window delimited between two triggering events.

12. An electronic apparatus, comprising:
a health monitoring device, including:
a semiconductor die, including:
an electric potential sensor configured to detect potential variations present on a body of a living being and associated with a heart rhythm and to generate a cardiac signal; and
cardiac parameter determination circuitry configured to receive the cardiac signal and determine cardiac parameters indicative of a health state,
wherein the cardiac parameter determination circuitry is configured to detect triggering events including threshold exceeding and to determine features of the cardiac signal in time windows defined by the triggering events and to detect a time distance between two triggering events exceeding the threshold; and
one or more electrodes configured to detect the cardiac signal, the electrodes electrically coupled to the electric potential sensor.

13. The electronic apparatus according to claim 12, comprising a personal computer, wherein the one or more electrodes include a first and a second key of the personal computer.

14. The electronic apparatus according to claim 12, further comprising decision circuitry configured to receive the cardiac parameters and generate a health signal based on a comparison with threshold values.

15. A method of monitoring health using a health monitoring device integrated into a semiconductor material die, the method comprising:
detecting electric potential variations on a body of a living being and associated with a heart rhythm;
generating a cardiac signal;
determining cardiac parameters indicative of a health state on the basis of the cardiac signal;
wherein determining cardiac parameters includes detecting triggering events and detecting features of the cardiac signal in time windows defined by the triggering events;
receiving a sequence of samples of the cardiac signal;
detecting a first exceeding of a first threshold of the cardiac signal by a first peak sample of the sequence of samples;
initiating a first counter upon detecting the first exceeding of the first threshold;
detecting a second exceeding of the first threshold of the cardiac signal by a second peak sample of the sequence of samples; and
acquiring a count value of the first counter upon detecting the second exceeding.

16. The health monitoring method according to claim 15, further comprising receiving cardiac parameters and generating a health signal based on a comparison with threshold values.

17. The health monitoring method according to claim 15, wherein generating the cardiac signal includes generating a digital signal including the sequence of samples and detecting cardiac parameters includes detecting the heart rate.

18. The health monitoring method according to claim 15, comprising:
generating an inertial signal through a MEMS movement sensor;
detecting movement parameters of the inertial signal;
detecting a movement condition or a rest condition from the movement parameters;
generating a movement signal in response to detection of the movement condition; and
providing a health state information based on the cardiac parameters in response to detection of the rest condition.

19. The health monitoring method according to claim 15, comprising:
receiving an input signal;
detecting at least one of the following triggering events of the input signal:
a) detecting when the input signal goes from negative to positive and generating a positive zero-crossing event;
b) detecting when the input signal goes from positive to negative and generating a negative zero-crossing event;
c) detecting when the input signal assumes a maximum or minimum value and generating a peak event;
d) detecting when the input signal assumes a maximum value and generating a maximum event; or
e) generating a clock event CKT,
and detecting at least one of the following features of the input signal:
f) calculating the mean of values of the input signal in a window delimited between two triggering events St;
g) calculating the variance of the input signal between two triggering events;
h) calculating the energy of the input signal within a window delimited between two triggering events or a window of predetermined duration from a triggering event;

i) calculating the difference between the maximum value and the minimum value of the input signal in a window delimited between two triggering events or in a window of predetermined duration from a triggering event;
j) calculating the number of negative crossings in a window delimited between two triggering events or in a window of predetermined duration from a triggering event;
k) calculating the peak number of the input signal in a window delimited between two triggering events;
l) calculating the positive peak number of the input signal in a window delimited between two triggering events;
m) calculating the negative peak number of the input signal in a window delimited between two triggering events;
n) detecting the minimum value of the input signal in a window delimited between two triggering events;
o) detecting the maximum value of the input signal in a window delimited between two triggering events; or
p) calculating the duration of the input signal in a window delimited between two triggering events.

* * * * *